United States Patent
Watson et al.

(10) Patent No.: US 9,451,887 B2
(45) Date of Patent: Sep. 27, 2016

(54) SYSTEMS AND METHODS FOR MEASURING ELECTROMECHANICAL DELAY OF THE HEART

(75) Inventors: James N. Watson, Fife (GB); Paul Stanley Addison, Midlothian (GB); Robert Stoughton, Boulder, CO (US)

(73) Assignee: Nellcor Puritan Bennett Ireland, Galway (IE)

( * ) Notice: Subject to any disclaimer, the term of this patent is extended or adjusted under 35 U.S.C. 154(b) by 919 days.

(21) Appl. No.: 12/751,814

(22) Filed: Mar. 31, 2010

(65) Prior Publication Data

US 2011/0245690 A1    Oct. 6, 2011

(51) Int. Cl.
| | |
|---|---|
| *A61B 5/02* | (2006.01) |
| *A61B 5/024* | (2006.01) |
| *A61B 5/022* | (2006.01) |
| *A61B 5/0402* | (2006.01) |
| *A61B 5/00* | (2006.01) |

(52) U.S. Cl.
CPC .......... *A61B 5/02416* (2013.01); *A61B 5/022* (2013.01); *A61B 5/0402* (2013.01); *A61B 5/6814* (2013.01); *A61B 5/6816* (2013.01); *A61B 5/6823* (2013.01); *A61B 5/6824* (2013.01); *A61B 5/6826* (2013.01)

(58) Field of Classification Search
CPC .. A61B 5/021; A61B 5/024; A61B 5/02438; A61B 5/026; A61B 5/028; A61B 5/0535; A61B 5/022; A61B 5/0002; A61B 5/14532; A61B 5/1455; A61B 5/14551; A61B 5/02416; A61B 5/02154; A61B 5/441; A61B 5/0205

USPC ........................................................ 600/500
See application file for complete search history.

(56) References Cited

U.S. PATENT DOCUMENTS

| | | |
|---|---|---|
| 3,835,840 A | 9/1974 | Mount |
| 4,561,447 A | 12/1985 | Kawamura et al. |
| 4,676,253 A | 6/1987 | Newman |
| 4,729,382 A | 3/1988 | Schaffer |
| 4,802,486 A | 2/1989 | Goodman et al. |
| 4,830,017 A | 5/1989 | Perry |

(Continued)

FOREIGN PATENT DOCUMENTS

| | | |
|---|---|---|
| EP | 0443267 | 8/1991 |
| EP | 0755221 | 1/1997 |

(Continued)

OTHER PUBLICATIONS

Bank, Alan J., Kaiser, Daniel R., "Smooth Muscle Relaxation: Effects on Arterial Compliance, Distensibility, Elastic modulus, and Pulse Wave Velocity," Hypertension, vol. 32, No. 2, Aug. 1998, pp. 356-359.

(Continued)

*Primary Examiner* — Patricia Mallari
*Assistant Examiner* — Vasuda Ramachandran
(74) *Attorney, Agent, or Firm* — Shvarts & Leiz LLP

(57) ABSTRACT

Systems and methods are disclosed herein for measuring the electromechanical delay of the heart of a patient. An electrocardiogram (EKG) signal may be used to detect heart electrical activity. Photoplethysmograph (PPG) signals may be used to detect heart mechanical activity. The electromechanical delay may be calculated based at least in part on the timing of an EKG signal and at least two PPG signals.

23 Claims, 8 Drawing Sheets

(56) References Cited

U.S. PATENT DOCUMENTS

| | | |
|---|---|---|
| 4,836,213 A | 6/1989 | Wenzel et al. |
| 4,854,327 A | 8/1989 | Kunig |
| 4,898,176 A | 2/1990 | Petre |
| 4,924,871 A | 5/1990 | Honeyager |
| 4,928,692 A | 5/1990 | Goodman et al. |
| 4,928,700 A | 5/1990 | Harada |
| 4,951,679 A | 8/1990 | Harada |
| 4,976,268 A | 12/1990 | Kurosawa et al. |
| 4,987,900 A | 1/1991 | Eckerle |
| 5,065,765 A | 11/1991 | Eckerle |
| 5,099,841 A | 3/1992 | Heinonen et al. |
| 5,103,831 A | 4/1992 | Niwa |
| 5,105,815 A | 4/1992 | Hall et al. |
| 5,119,824 A | 6/1992 | Niwa |
| 5,131,400 A | 7/1992 | Harada |
| 5,163,328 A | 11/1992 | Holland |
| 5,170,796 A | 12/1992 | Kobayashi |
| 5,176,143 A | 1/1993 | Eckerle et al. |
| 5,178,154 A | 1/1993 | Ackmann et al. |
| 5,179,956 A | 1/1993 | Harada et al. |
| 5,204,922 A | 4/1993 | Weir |
| 5,238,000 A | 8/1993 | Niwa |
| 5,241,964 A | 9/1993 | McQuilkin |
| 5,255,686 A | 10/1993 | Takeda et al. |
| 5,269,312 A | 12/1993 | Kawamura et al. |
| 5,289,823 A | 3/1994 | Eckerle |
| 5,309,917 A | 5/1994 | Wang |
| 5,431,159 A | 7/1995 | Baker |
| 5,450,852 A | 9/1995 | Archibald et al. |
| 5,467,771 A | 11/1995 | Narimatsu |
| 5,490,506 A | 2/1996 | Takatani |
| 5,494,043 A | 2/1996 | O'Sullivan et al. |
| 5,497,779 A | 3/1996 | Takaya |
| 5,505,209 A | 4/1996 | Reining |
| 5,533,511 A | 7/1996 | Kaspari |
| 5,535,753 A | 7/1996 | Petrucelli et al. |
| 5,562,621 A | 10/1996 | Claude et al. |
| 5,564,427 A | 10/1996 | Aso et al. |
| 5,575,284 A | 11/1996 | Athan |
| 5,617,868 A | 4/1997 | Harada |
| 5,640,964 A | 6/1997 | Archibald et al. |
| 5,649,542 A | 7/1997 | Archibald et al. |
| 5,649,543 A | 7/1997 | Hosaka et al. |
| 5,662,106 A * | 9/1997 | Swedlow et al. ............ 600/331 |
| 5,676,140 A | 10/1997 | Ukawa |
| 5,682,898 A | 11/1997 | Aung |
| 5,685,316 A | 11/1997 | Schookin et al. |
| 5,704,362 A | 1/1998 | Hersh et al. |
| 5,709,212 A | 1/1998 | Sugo |
| 5,720,292 A | 2/1998 | Poliac |
| 5,722,414 A | 3/1998 | Archibald et al. |
| 5,738,103 A | 4/1998 | Poliac |
| 5,743,856 A | 4/1998 | Oka et al. |
| 5,755,669 A | 5/1998 | Ono et al. |
| 5,762,610 A | 6/1998 | Narimatsu |
| 5,772,601 A | 6/1998 | Oka |
| 5,772,602 A | 6/1998 | Sakai |
| 5,776,071 A | 7/1998 | Inukai |
| 5,785,659 A | 7/1998 | Caro et al. |
| 5,791,347 A | 8/1998 | Flaherty et al. |
| 5,797,395 A | 8/1998 | Martin |
| 5,797,850 A | 8/1998 | Archibald et al. |
| 5,810,736 A | 9/1998 | Pail |
| 5,827,181 A | 10/1998 | Dias |
| 5,830,131 A | 11/1998 | Caro et al. |
| 5,832,924 A | 11/1998 | Archibald et al. |
| 5,833,618 A | 11/1998 | Caro |
| 5,848,970 A | 12/1998 | Voss |
| 5,857,975 A | 1/1999 | Golub |
| 5,873,834 A | 2/1999 | Yanagi et al. |
| 5,904,654 A | 5/1999 | Wohltmann et al. |
| 5,941,828 A | 8/1999 | Archibald et al. |
| 5,964,711 A | 10/1999 | Voss |
| 6,002,952 A | 12/1999 | Diab |
| 6,004,274 A | 12/1999 | Nolan |
| 6,007,492 A | 12/1999 | Goto et al. |
| 6,011,986 A | 1/2000 | Diab et al. |
| 6,022,320 A | 2/2000 | Ogura |
| 6,027,452 A | 2/2000 | Flaherty et al. |
| 6,027,453 A | 2/2000 | Miwa |
| 6,027,455 A | 2/2000 | Inukai et al. |
| 6,045,509 A | 4/2000 | Caro et al. |
| 6,067,462 A | 5/2000 | Diab |
| 6,083,171 A | 7/2000 | Ono et al. |
| 6,095,987 A | 8/2000 | Shmulewitz |
| 6,135,966 A | 10/2000 | Ko |
| 6,157,850 A | 12/2000 | Diab et al. |
| 6,159,157 A | 12/2000 | Archibald et al. |
| 6,161,038 A | 12/2000 | Schookin et al. |
| 6,186,954 B1 | 2/2001 | Narimatsu |
| 6,186,955 B1 | 2/2001 | Baura |
| 6,190,382 B1 | 2/2001 | Ormsby et al. |
| 6,196,974 B1 | 3/2001 | Miwa |
| 6,217,524 B1 | 4/2001 | Orr et al. |
| 6,227,196 B1 | 5/2001 | Jaffe et al. |
| 6,228,034 B1 | 5/2001 | Voss et al. |
| 6,241,661 B1 | 6/2001 | Schluess et al. |
| 6,241,679 B1 | 6/2001 | Curran |
| 6,245,022 B1 | 6/2001 | Archibald et al. |
| 6,251,081 B1 | 6/2001 | Narimatsu |
| 6,263,222 B1 | 7/2001 | Diab et al. |
| 6,292,689 B1 | 9/2001 | Wallace |
| 6,293,915 B1 | 9/2001 | Amano et al. |
| 6,299,582 B1 | 10/2001 | Brockway et al. |
| 6,332,867 B1 | 12/2001 | Chen et al. |
| 6,350,242 B1 | 2/2002 | Doten et al. |
| 6,371,921 B1 | 4/2002 | Caro |
| 6,443,905 B1 | 9/2002 | Nissila et al. |
| 6,463,311 B1 | 10/2002 | Diab |
| 6,471,646 B1 | 10/2002 | Thede |
| 6,471,655 B1 | 10/2002 | Baura |
| 6,506,161 B2 | 1/2003 | Brockway et al. |
| 6,514,211 B1 | 2/2003 | Baura |
| 6,524,240 B1 | 2/2003 | Thede |
| 6,561,986 B2 | 5/2003 | Baura |
| 6,589,185 B1 | 7/2003 | Archibald et al. |
| 6,599,251 B2 * | 7/2003 | Chen et al. ............... 600/485 |
| 6,602,199 B2 | 8/2003 | Chen et al. |
| 6,602,201 B1 | 8/2003 | Hepp et al. |
| 6,606,511 B1 | 8/2003 | Ali et al. |
| 6,626,839 B2 | 9/2003 | Doten et al. |
| 6,631,281 B1 | 10/2003 | Kastle |
| 6,645,156 B2 | 11/2003 | Oka |
| 6,658,277 B2 | 12/2003 | Wasserman |
| 6,684,090 B2 | 1/2004 | Ali et al. |
| RE38,476 E | 3/2004 | Diab et al. |
| 6,699,194 B1 | 3/2004 | Diab |
| 6,719,705 B2 | 4/2004 | Mills |
| 6,767,328 B2 | 7/2004 | Kulik |
| 6,773,397 B2 | 8/2004 | Kelly |
| 6,783,498 B2 | 8/2004 | Sackner |
| 6,816,741 B2 | 11/2004 | Diab |
| 6,822,564 B2 | 11/2004 | Al-Ali |
| 6,826,419 B2 | 11/2004 | Diab |
| 6,827,688 B2 | 12/2004 | Goto et al. |
| 6,852,083 B2 | 2/2005 | Caro |
| 6,855,112 B2 | 2/2005 | Kao |
| 6,863,652 B2 | 3/2005 | Huang et al. |
| 6,869,403 B2 | 3/2005 | Narimatsu et al. |
| 6,929,610 B2 | 8/2005 | Forstner |
| 6,996,427 B2 | 2/2006 | Ali et al. |
| 7,004,907 B2 | 2/2006 | Banet |
| 7,043,293 B1 | 5/2006 | Baura |
| 7,044,918 B2 | 5/2006 | Diab |
| 7,070,566 B2 | 7/2006 | Medero et al. |
| 7,074,192 B2 | 7/2006 | Friedman et al. |
| 7,079,035 B2 | 7/2006 | Bock et al. |
| 7,087,025 B2 | 8/2006 | Baruch |
| 7,184,809 B1 | 2/2007 | Sterling |
| 7,215,984 B2 | 5/2007 | Diab et al. |
| 7,215,986 B2 | 5/2007 | Diab et al. |
| 7,252,636 B2 | 8/2007 | Brown |
| 7,320,030 B2 | 1/2008 | Brown |
| 7,335,162 B2 | 2/2008 | Eide |

(56) References Cited

U.S. PATENT DOCUMENTS

| | | |
|---|---|---|
| 7,376,238 B1 | 5/2008 | Rivas et al. |
| 7,390,300 B2 | 6/2008 | Inukai |
| 7,390,301 B2 | 6/2008 | Skrabal |
| 7,393,327 B2 | 7/2008 | Inukai |
| 7,400,257 B2 | 7/2008 | Rivas |
| 7,455,643 B1 | 11/2008 | Li et al. |
| 7,481,772 B2 | 1/2009 | Banet |
| 7,485,095 B2 | 2/2009 | Shusterman |
| 2005/0148885 A1 | 7/2005 | Tweed et al. |
| 2005/0251344 A1 | 11/2005 | Appel et al. |
| 2005/0261594 A1 | 11/2005 | Banet |
| 2006/0009700 A1 | 1/2006 | Brumfield et al. |
| 2006/0063992 A1 | 3/2006 | Yu et al. |
| 2006/0063993 A1 | 3/2006 | Yu et al. |
| 2006/0079945 A1 | 4/2006 | Libbus |
| 2006/0206021 A1 | 9/2006 | Diab |
| 2006/0217614 A1 | 9/2006 | Takala et al. |
| 2006/0217628 A1 | 9/2006 | Huiku |
| 2006/0241975 A1 | 10/2006 | Brown |
| 2006/0285736 A1 | 12/2006 | Brown |
| 2006/0287603 A1 | 12/2006 | Bartnik et al. |
| 2007/0066910 A1 | 3/2007 | Inukai et al. |
| 2007/0083093 A1 | 4/2007 | Diab |
| 2007/0118045 A1 | 5/2007 | Naghavi et al. |
| 2007/0225582 A1 | 9/2007 | Diab et al. |
| 2007/0225609 A1 | 9/2007 | Rosch et al. |
| 2007/0249467 A1 | 10/2007 | Hong et al. |
| 2007/0276632 A1* | 11/2007 | Banet et al. .................. 702/187 |
| 2008/0015451 A1 | 1/2008 | Hatib et al. |
| 2008/0030468 A1 | 2/2008 | Ali et al. |
| 2008/0033305 A1 | 2/2008 | Hatib et al. |
| 2008/0132798 A1 | 6/2008 | Hong et al. |
| 2008/0183083 A1 | 7/2008 | Markowitz et al. |
| 2008/0214903 A1 | 9/2008 | Orbach |
| 2008/0214942 A1 | 9/2008 | Oh et al. |
| 2008/0221461 A1 | 9/2008 | Zhou et al. |
| 2008/0242955 A1 | 10/2008 | Uutela et al. |
| 2008/0262362 A1 | 10/2008 | Kolluri et al. |
| 2009/0048497 A1 | 2/2009 | Keren |
| 2009/0187110 A1* | 7/2009 | Voss et al. .................. 600/500 |
| 2009/0326386 A1 | 12/2009 | Sethi et al. |
| 2009/0326393 A1 | 12/2009 | Sethi et al. |
| 2010/0081945 A1 | 4/2010 | Sethi et al. |
| 2011/0021929 A1 | 1/2011 | Sethi et al. |

FOREIGN PATENT DOCUMENTS

| | | |
|---|---|---|
| GB | 2 356 250 | 5/2001 |
| GB | 2 356 251 | 5/2001 |
| GB | 2 356 252 | 5/2001 |
| JP | 03-231630 | 10/1991 |
| JP | 06-142082 | 5/1994 |
| JP | 07-136136 | 5/1995 |
| JP | 03-225268 | 12/2003 |
| WO | WO 03/084396 | 10/2003 |

OTHER PUBLICATIONS

Berne, Robert M., Levy, Matthew N., eds., Physiology, 2nd edition, St. Louis, Mosby, 1988, pp. 357-681.

Finkelstein, Stanley M., Cohn, Jay N., "First- and Third-Order Models for Determining Arterial Compliance," Journal of Hypertension, vol. 10, supplement 6, Aug. 1992, pp. S11-S14.

Fitchett, D., Bouthier, JD, Simon, A. Ch., Levenson, JA, Safar, ME, "Forearm Arterial Compliance: The Validation of a Plethysmographic Technique for the Measurement of Arterial Compliance," Clinical Science, vol. 67, No. 1, Jul. 1984, pp. 69-72.

Fletcher, Gerald F., ed., Cardiovascular Response to Exercise, Mt. Kisco, NY, Futura Publishing Co., 1994.

Fung, YC, Biomechanics: Circulation, 2nd Edition, New York, Springer, 1997.

Geddes, LA, Handbook of Blood Pressure Measurement, Clifton, New Jersey, Humana Press, 1991.

Millasseau, Sandrine C, Guigui, Franck G, Kelly, Ronan P., Prasad, Krishna, Cockcroft, John R., Ritter, James M., Chowienczyk, Philip J., Noninvasive Assessment of the Digital Volume Pulse: Comparison with the Peripheral Pressure Pulse, Hypertension, vol. 36, No. 6, Dec. 2000, pp. 952-956.

Moyle, John TB, Hahn, CEW, Adams, Anthony P, Pulse Oximetry, Revised Edition, London, BMJ, 1998.

Nara, Andrew R., Burns, Michael P., Downs, W. Gregory, Blood Pressure, Redmond, Washington, SpaceLabs, 1989.

Nichols, Wilmer W., O'Rourke, Michael F., McDonald's Blood Flow in Arteries: Theoretic, Experimental, and Clinical Principles, 3rd Edition, Philadelphia, Lea & Febiger, 1990.

O'Rourke, Michael F., Gallagher, David E., "Pulse Wave Analysis," Journal of Hypertension, vol. 14, supplement 5, Dec. 1996, pp. S147-S157.

Takazawa, Kenji, Tanaka, Nobuhiro, Fujita, Masami, Matsuoka, Osamu, Saiki, Tokuyu, Aikawa, Masaru, Tamura, Sinobu, Ibukiyama, Chiharu, "Assessment of Vasoactive Agents and Vascular Aging by the Second Derivative of Photoplethysmogram Waveform," Hypertension, vol. 32, No. 2, Aug. 1998, pp. 365-370.

Tardy, Y, Meister, JJ, Perret F, Brunner, HR, Arditi, M, "Non-Invasive Estimate of the Mechanical Properties of Peripheral Arteries from Ultrasonic and Photoplethysmographic Measurements," Clinical Physics and Physiological Measurement, vol. 12, No. 1, pp. 39-54, Feb. 1991.

Young, Christopher C., Mark, Jonathan B., White, William, DeBree, Ashley, Vender, Jeffery S., Fleming, Andrew, "Clinical Evaluation of Continuous Noninvasive Blood Pressure Monitoring: Accuracy and Tracking Capabilities," Journal of Clinical Monitoring, vol. 11, No. 4, Jul. 1995, pp. 245-252.

* cited by examiner

SYSTEMS AND METHODS FOR MEASURING ELECTROMECHANICAL DELAY OF THE HEART

SUMMARY

The present disclosure relates to signal processing and, more particularly, the present disclosure relates to systems and methods for measuring the electromechanical delay of the heart of a patient. An electrocardiogram (EKG) signal may be used to detect heart electrical activity. Photoplethysmograph (PPG) signals may be used to detect heart mechanical activity. The electromechanical delay may be calculated based at least in part on the timing of an EKG signal and at least two PPG signals.

The disclosure relates to systems and methods for measuring electromechanical delay of the heart of a patient. At least two probes and/or sensors attached to a patient are used to generated photoplethysmograph (PPG) signals. An electrocardiogram (EKG) probe and/or sensor attached to the patient are used to generate an EKG signal. A processor for calculating the electromechanical delay of the heart of a patient is coupled to the PPG signal generator and the EKG signal generator. The processor is capable of determining differential pulse transit time (DPTT) values based at least in part on the PPG signals. The processor is also capable of determining an EKG to PPG transit time value based at least in part on the EKG signal and one of the PPG signals. The processor is then capable of calculating an electromechanical delay value based at least in part on the determined DPTT value and EKG to PPG transit time value.

In an embodiment, the EKG to PPG transit time values may include a substantially constant electromechanical delay component and a variable pulse transit time component. The variable pulse transit time component may scale substantially linearly with DPTT. In an embodiment, the relationship between the EKG to PPG transit time and DPTT is $E = A \cdot T + D$ or a mathematical equivalent thereof, wherein E is an EKG to PPG transit time value, T is a DPTT value, D is the electromechanical delay value, and A is a constant.

In an embodiment, the processor is further capable of determining a further EKG to PPG transit time value based at least in part on the EKG signal and a second PPG signal. The processor is then capable of calculating an electromechanical delay value based at least in part on the DPTT value and the further EKG to PPG transit time value. In an embodiment, the processor is further capable of calculating an electromechanical delay value based at least in part on the DPTT value and the EKG to PPG transit time values determined from both the first and the second PPG signal.

In an embodiment, the processor is further capable of assessing a condition of the patient's heart based at least in part on the electromechanical delay value. The processor is capable of monitoring the electromechanical delay value over time, determining a change in the electromechanical delay value, and triggering the output device to generate an alert.

In an embodiment, the processor is further capable of calculating a blood pressure value of the patient based on at least one of: (a) the differential pulse transit time values and (b) the electromechanical delay value and EKG to PPG transit time values. In response to detecting a signal degradation of at least one PPG signal, the processor is further capable of calculating a blood pressure value of the patient based on the electromechanical delay value and EKG to PPG transit time values from at least one other PPG signal.

BRIEF DESCRIPTION OF THE DRAWINGS

The above and other features of the present disclosure, its nature and various advantages will be more apparent upon consideration of the following detailed description, taken in conjunction with the accompanying drawings in which.

DETAILED DESCRIPTION

Figure 1:
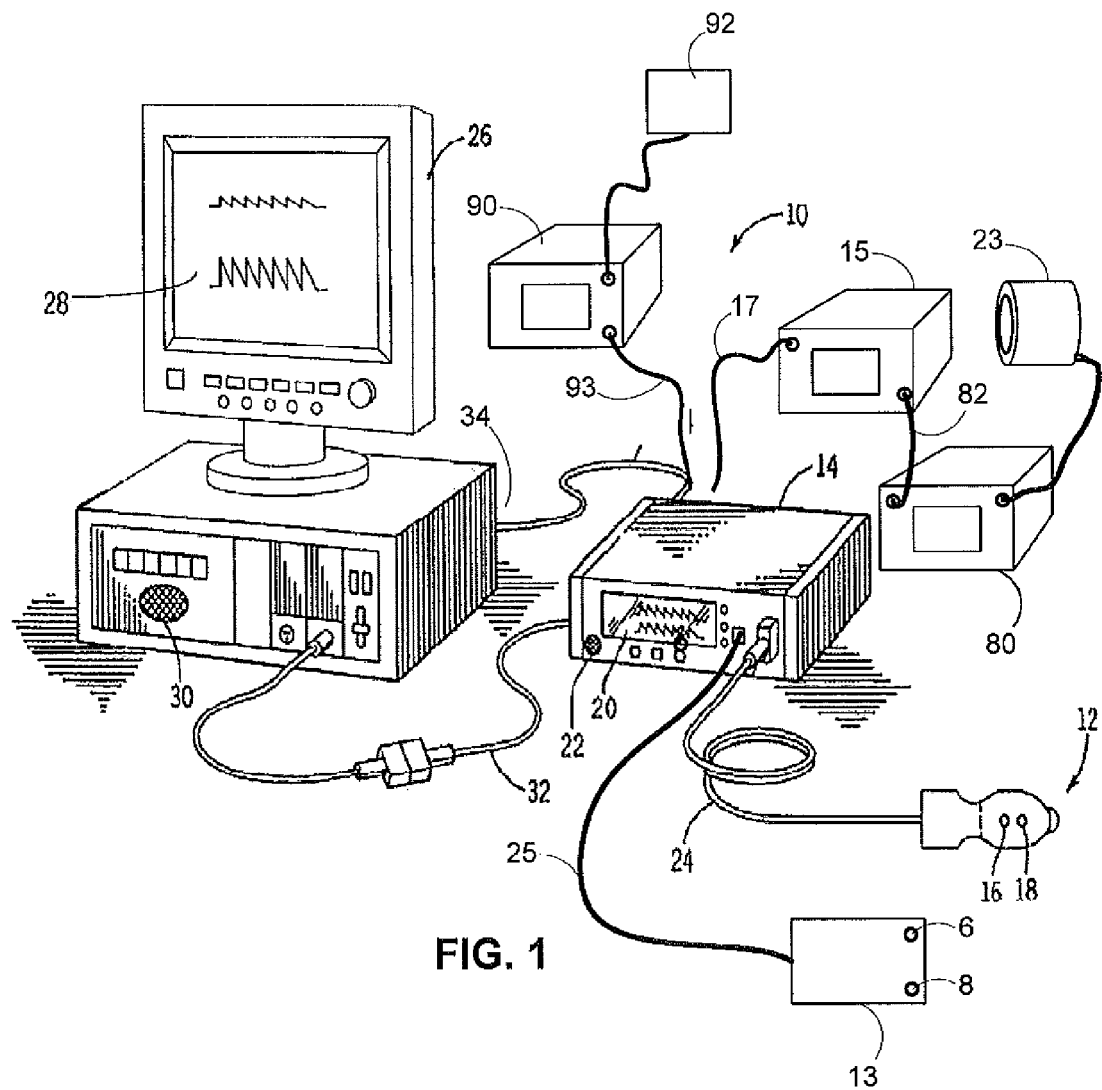
FIG. 1 shows an illustrative pulse oximetry system in accordance with an embodiment.

An oximeter is a medical device that may determine the oxygen saturation of the blood. One common type of oximeter is a pulse oximeter, which may indirectly measure the oxygen saturation of a patient's blood (as opposed to measuring oxygen saturation directly by analyzing a blood sample taken from the patient) and changes in blood volume in the skin. Ancillary to the blood oxygen saturation measurement, pulse oximeters may also be used to measure the pulse rate of the patient. Pulse oximeters typically measure and display various blood flow characteristics including, but not limited to, the oxygen saturation of hemoglobin in arterial blood.

An oximeter may include a light sensor that is placed at a site on a patient, typically a fingertip, toe, forehead or earlobe, or in the case of a neonate, across a foot. The oximeter may pass light using a light source through blood perfused tissue and photoelectrically sense the absorption of light in the tissue. In addition, locations which are not typically understood to be optimal for pulse oximetry serve as suitable sensor locations for the blood pressure monitoring processes described herein, including any location on the body that has a strong pulsatile arterial flow. For example, additional suitable sensor locations include, without limitation, the neck to monitor cartoid artery pulsatile flow, the wrist to monitor radial artery pulsatile flow, the inside of a patient's thigh to monitor femural artery pulsatile flow, the ankle to monitor tibial artery pulsatile flow, and around or in front of the ear. Suitable sensors for these locations may include sensors for sensing absorbed light based on detecting reflected light. In all suitable locations, for example, the oximeter may measure the intensity of light that is received at the light sensor as a function of time. The oximeter may also include sensors at multiple locations. A signal representing light intensity versus time or a mathematical manipulation of this signal (e.g., a scaled version thereof, a log taken thereof, a scaled version of a log taken thereof, etc.) may be referred to as the photoplethysmograph (PPG) signal. In addition, the term "PPG signal," as used herein, may also refer to an absorption signal (i.e., representing the amount of light absorbed by the tissue) or any suitable mathematical manipulation thereof. The light intensity or the amount of light absorbed may then be used to calculate the amount of the blood constituent (e.g., oxyhemoglobin) being measured as well as the pulse rate and when each individual pulse occurs.

The light passed through the tissue is selected to be of one or more wavelengths that are absorbed by the blood in an amount representative of the amount of the blood constituent present in the blood. The amount of light passed through the tissue varies in accordance with the changing amount of blood constituent in the tissue and the related light absorption. Red and infrared wavelengths may be used because it has been observed that highly oxygenated blood will absorb relatively less red light and more infrared light than blood with a lower oxygen saturation. By comparing the intensities of two wavelengths at different points in the pulse cycle, it is possible to estimate the blood oxygen saturation of hemoglobin in arterial blood.

FIG. 1 is a perspective view of an embodiment of a pulse oximetry system 10 that may be used to measure electro-mechanical delay of the heart of a patient and that also may be used for continuous non-invasive blood pressure (CNIBP) monitoring. System 10 may include sensors 12 and 13 and a pulse oximetry monitor 14. Sensor 12 may include an emitter 16 for emitting light at two or more wavelengths into a patient's tissue. A detector 18 may also be provided in sensor 12 for detecting the light originally from emitter 16 that emanates from the patient's tissue after passing through the tissue. Similarly, sensor 13 may include an emitter 6 and a detector 8, which may operate in a fashion similar to that of emitter 16 and detector 18, respectively.

According to an embodiment and as will be described, system 10 may include a plurality of sensors forming a sensor array in lieu of either or both of sensors 12 and 13. Each of the sensors of the sensor array may be a complementary metal oxide semiconductor (CMOS) sensor. Alternatively, each sensor of the array may be charged coupled device (CCD) sensor. In an embodiment, the sensor array may be made up of a combination of CMOS and CCD sensors. The CCD sensor may comprise a photoactive region and a transmission region for receiving and transmitting data whereas the CMOS sensor may be made up of an integrated circuit having an array of pixel sensors. Each pixel may have a photodetector and an active amplifier.

According to an embodiment, emitter 16 and detector 18 may be on opposite sides of a digit such as a finger or toe, in which case the light that is emanating from the tissue has passed completely through the digit. In an embodiment, emitter 16 and detector 18 may be arranged so that light from emitter 16 penetrates the tissue and is reflected by the tissue into detector 18, such as a sensor designed to obtain pulse oximetry data from a patient's forehead. Similarly, according to an embodiment, emitter 6 and detector 8 may be on opposite sides of an ear (e.g., positioned on opposite sides of a patient's earlobe). In an embodiment, emitter 6 and detector 8 may be arranged so that light from emitter 6 penetrates the tissue and is reflected by the tissue into detector 8, such as a sensor designed to obtain pulse oximetry data from a patient's forehead.

In an embodiment, the sensors or sensor array may be connected to and draw its power from monitor 14 as shown. In another embodiment, the sensors may be wirelessly connected to monitor 14 and include their own battery or similar power supply (not shown). Monitor 14 may be configured to calculate physiological parameters based at least in part on data received from sensors 12 and 13 relating to light emission and detection. In an alternative embodiment, the calculations may be performed on the monitoring device itself and the result of the oximetry reading may be passed to monitor 14. Further, monitor 14 may include a display 20 configured to display the physiological parameters or other information about the system. In the embodiment shown, monitor 14 may also include a speaker 22 to provide an audible sound that may be used in various other embodiments, such as for example, sounding an audible alarm in the event that a patient's physiological parameters are not within a predefined normal range. In an embodiment, monitor 14 may include a blood pressure monitor 15. In alternative embodiments, the pulse oximetry system 10 may include a stand alone blood pressure monitor 15 in communication with the monitor 14 via a cable 17 or a wireless network link.

In an embodiment, sensors 12 and 13, or the sensor array, may be communicatively coupled to monitor 14 via a cables 24 and 25, respectively. However, in other embodiments, a wireless transmission device (not shown) or the like may be used instead of or in addition to cables 24 and 25.

In the illustrated embodiment, pulse oximetry system 10 may also include a multi-parameter patient monitor 26. The monitor may be cathode ray tube type, a flat panel display (as shown) such as a liquid crystal display (LCD) or a plasma display, or any other type of monitor now known or later developed. Multi-parameter patient monitor 26 may be configured to calculate physiological parameters and to provide a display 28 for information from monitor 14 and from other medical monitoring devices or systems (not shown). For example, multiparameter patient monitor 26 may be configured to display an estimate of a patient's blood oxygen saturation generated by pulse oximetry monitor 14 (referred to as an "SpO$_2$" measurement), pulse rate information from monitor 14 and blood pressure from blood pressure monitor 15 on display 28.

Monitor 14 may be communicatively coupled to multi-parameter patient monitor 26 via a cable 32 or 34 that is coupled to a sensor input port or a digital communications port, respectively and/or may communicate wirelessly (not shown). In addition, monitor 14 and/or multi-parameter patient monitor 26 may be coupled to a network to enable the sharing of information with servers or other workstations (not shown). Monitor 14 may be powered by a battery (not shown) or by a conventional power source such as a wall outlet.

Calibration device 80, which may be powered by monitor 14, a battery, or by a conventional power source such as a wall outlet, may include any suitable blood pressure calibration device. For example, calibration device 80 may take the form of any invasive or non-invasive blood pressure monitoring or measuring system used to generate reference blood pressure measurements for use in calibrating the CNIBP monitoring techniques described herein. Such calibration devices may include, for example, an aneroid or mercury sphygmomanometer and occluding cuff 23, a pressure sensor inserted directly into a suitable artery of a patient, an oscillometric device or any other device or mechanism used to sense, measure, determine, or derive a reference blood pressure measurement. In some embodiments, calibration device 80 may include a manual input device (not shown) used by an operator to manually input reference blood pressure measurements obtained from some other source (e.g., an external invasive or non-invasive blood pressure measurement system).

Calibration device 80 may also access reference blood pressure measurements stored in memory (e.g., RAM, ROM, or a storage device). For example, in some embodiments, calibration device 80 may access reference blood pressure measurements from a relational database stored within calibration device 80, monitor 14, monitor 15, or multi-parameter patient monitor 26. The reference blood pressure measurements generated or accessed by calibration device 80 may be updated in real-time, resulting in a continuous source of reference blood pressure measurements for use in continuous or periodic calibration. Alternatively, reference blood pressure measurements generated or accessed by calibration device 80 may be updated periodically, and calibration may be performed on the same periodic cycle. In the depicted embodiments, calibration device 80 is connected to monitor 14 or blood pressure monitor 15 via cable 82. In other embodiments, calibration device 80 may be a stand-alone device that may be in wireless communication with monitor 14 or blood pressure monitor 15. Reference blood pressure measurements may then be wirelessly transmitted to monitor 14 or monitor 15 for use in calibration. In still other embodiments, calibration device 80 is completely integrated within monitor 14 or monitor 15.

Electromechanical delay monitor 90, may be configured to measure and/or monitor the patient-dependent delay time resulting from the electromechanical activation of a patient's heart. Electromechanical delay monitor 90 may receive measurements of the electrical activation of a patient's heart using sensor 92. Sensor 92 may be, for example, an electrocardiogram (EKG) sensor, an array of EKG sensors, or any other suitable sensor or sensors that can detect the electrical activity of the heart. In an embodiment sensor 92 may be combined with and/or incorporated into a pulse oximetry sensor (e.g., sensors 12 and 13). Electromechanical delay monitor 90 may receive measurements of the mechanical activation of a patient's heart. Measurements of the mechanical activation of a patient's heart may be determined, for example, from one or more PPG signals obtained using sensors 12 and 13. Techniques for measuring the electromechanical delay of a patient's heart will be described in more detail below with respect to FIGS. 4-8.

Electromechanical delay monitor 90 may be powered by monitor 14, a battery, or by a conventional power source such as a wall outlet. In some embodiments, electromechanical delay monitor 90 may include a manual input device (not shown) used by an operator to manually input electromechanical delay measurements obtained from some other source. Electromechanical delay monitor 90 may also access electromechanical delay measurements stored in memory (e.g., RAM, ROM, or a storage device). For example, in some embodiments, electromechanical delay monitor 90 may access PPG signal data from a relational database stored within calibration device 80, monitor 14, or multi-parameter patient monitor 26. In the depicted embodiment, electromechanical delay monitor 90 is connected to monitor 14 via cable 93. In other embodiments, electromechanical delay monitor 90 may be a stand-alone device that may be in wireless communication with monitor 14. In still other embodiments, electromechanical delay monitor 90 may be completely integrated within monitor 14 or monitor 15.

Figure 2:
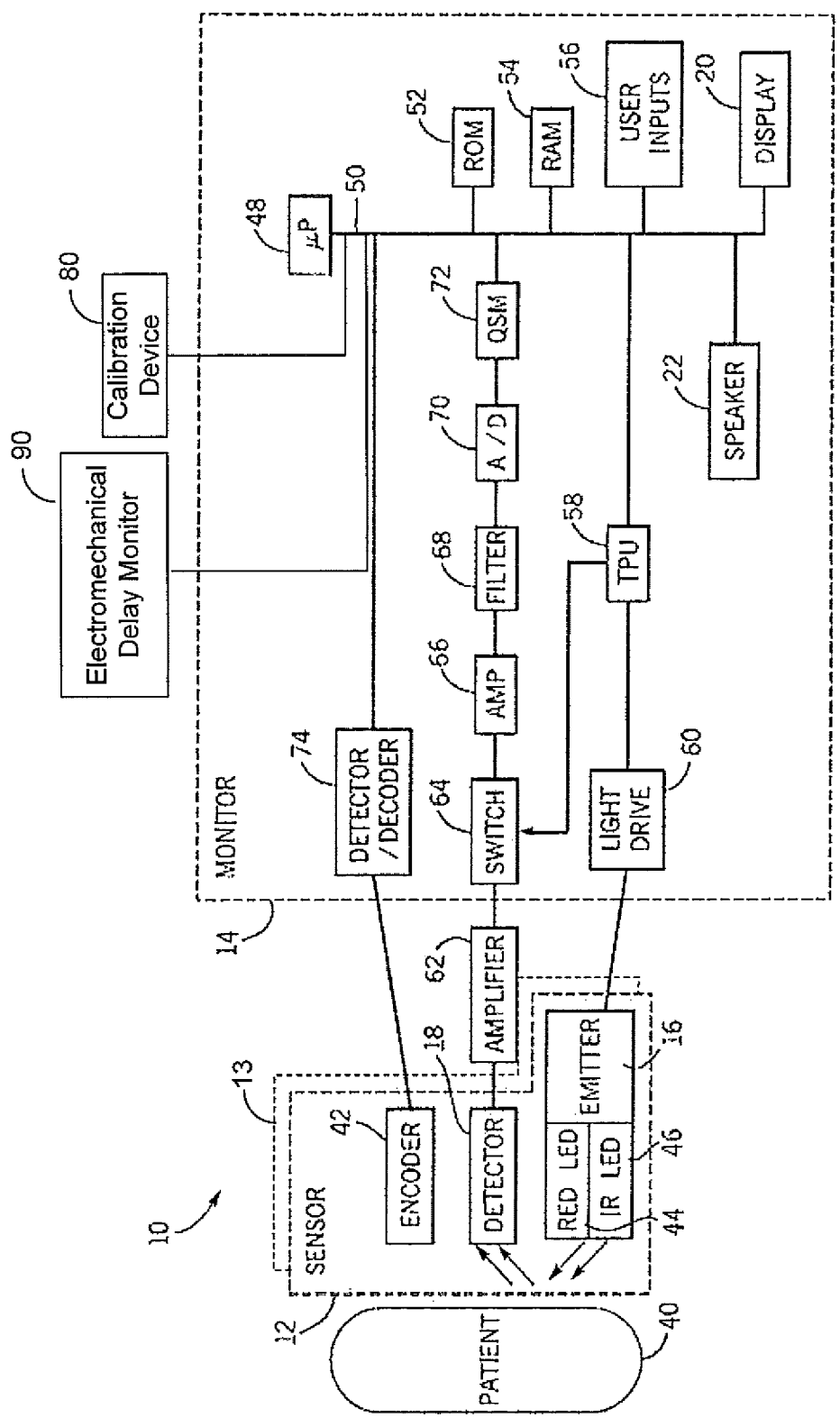
FIG. 2 is a block diagram of the illustrative pulse oximetry system of FIG. 1 coupled to a patient in accordance with an embodiment.

FIG. 2 is a block diagram of a pulse oximetry system, such as pulse oximetry system 10 of FIG. 1, which may be coupled to a patient 40 in accordance with an embodiment. Certain illustrative components of sensors 12 and 13 and monitor 14 are illustrated in FIG. 2. Because sensors 12 and 13 may include similar components and functionality, only sensor 12 will be discussed in detail for ease of illustration. It will be understood that any of the concepts, components, and operation discussed in connection with sensor 12 may be applied to sensor 13 as well (e.g., emitter 16 and detector 18 of sensor 12 may be similar to emitter 6 and detector 8 of sensor 13). Similarly, it will be understood that, as discussed in connection with FIG. 1, certain embodiments may use any suitable number of sensors or probes.

Sensor 12 may include emitter 16, detector 18, and encoder 42. In the embodiment shown, emitter 16 may be configured to emit at least two wavelengths of light (e.g., RED and IR) into a patient's tissue 40. Hence, emitter 16 may include a RED light emitting light source such as RED light emitting diode (LED) 44 and an IR light emitting light source such as IR LED 46 for emitting light into the patient's tissue 40 at the wavelengths used to calculate the patient's physiological parameters. In one embodiment, the RED wavelength may be between about 600 nm and about 700 nm, and the IR wavelength may be between about 800 nm and about 1000 nm. In embodiments where a sensor array is used in place of single sensor, each sensor may be configured to emit a single wavelength. For example, a first sensor emits only a RED light while a second only emits an IR light. In another example, the wavelengths of light used are selected based on the specific location of the sensor.

It will be understood that, as used herein, the term "light" may refer to energy produced by radiative sources and may include one or more of ultrasound, radio, microwave, millimeter wave, infrared, visible, ultraviolet, gamma ray or X-ray electromagnetic radiation. As used herein, light may also include any wavelength within the radio, microwave, infrared, visible, ultraviolet, or X-ray spectra, and that any suitable wavelength of electromagnetic radiation may be appropriate for use with the present techniques. Detector 18 may be chosen to be specifically sensitive to the chosen targeted energy spectrum of the emitter 16.

In an embodiment, detector 18 may be configured to detect the intensity of light at the RED and IR wavelengths. Alternatively, each sensor in the array may be configured to detect an intensity of a single wavelength. In operation, light may enter detector 18 after passing through the patient's tissue 40. Detector 18 may convert the intensity of the received light into an electrical signal. The light intensity is directly related to the absorbance and/or reflectance of light in the tissue 40. That is, when more light at a certain wavelength is absorbed or reflected, less light of that wavelength is received from the tissue by the detector 18. After converting the received light to an electrical signal, detector 18 may send the signal to monitor 14, where physiological parameters may be calculated based on the absorption of the RED and IR wavelengths in the patient's tissue 40.

In an embodiment, encoder 42 may contain information about sensor 12, such as what type of sensor it is (e.g., whether the sensor is intended for placement on a forehead or digit) and the wavelengths of light emitted by emitter 16. This information may be used by monitor 14 to select appropriate algorithms, lookup tables and/or calibration coefficients stored in monitor 14 for calculating the patient's physiological parameters.

Encoder 42 may contain information specific to patient 40, such as, for example, the patient's age, weight, and diagnosis. This information may allow monitor 14 to determine, for example, patient-specific threshold ranges in which the patient's physiological parameter measurements should fall and to enable or disable additional physiological parameter algorithms. Encoder 42 may, for instance, be a coded resistor which stores values corresponding to the type of sensor 12 or the type of each sensor in the sensor array, the wavelengths of light emitted by emitter 16 on each sensor of the sensor array, and/or the patient's characteristics. In another embodiment, encoder 42 may include a memory on which one or more of the following information may be stored for communication to monitor 14: the type of the sensor 12; the wavelengths of light emitted by emitter 16; the particular wavelength each sensor in the sensor array is monitoring; a signal threshold for each sensor in the sensor array; any other suitable information; or any combination thereof.

In an embodiment, signals from detector 18 and encoder 42 may be transmitted to monitor 14. In the embodiment shown, monitor 14 may include a general-purpose microprocessor 48 connected to an internal bus 50. Microprocessor 48 may be adapted to execute software, which may include an operating system and one or more applications, as part of performing the functions described herein. Also connected to bus 50 may be a read-only memory (ROM) 52, a random access memory (RAM) 54, user inputs 56, display 20, and speaker 22.

RAM 54 and ROM 52 are illustrated by way of example, and not limitation. Any suitable computer-readable media may be used in the system for data storage. Computer-readable media are capable of storing information that can be interpreted by microprocessor 48. This information may be data or may take the form of computer-executable instructions, such as software applications, that cause the microprocessor to perform certain functions and/or computer-implemented methods. Depending on the embodiment, such computer-readable media may include computer storage media and communication media. Computer storage media may include volatile and non-volatile, removable and non-removable media implemented in any method or technology for storage of information such as computer-readable instructions, data structures, program modules or other data. Computer storage media may include, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by components of the system.

In the embodiment shown, a time processing unit (TPU) 58 may provide timing control signals to a light drive circuitry 60, which may control when emitter 16 is illuminated and multiplexed timing for the RED LED 44 and the IR LED 46. TPU 58 may also control the gating-in of signals from detector 18 through an amplifier 62 and a switching circuit 64. These signals are sampled at the proper time, depending upon which light source is illuminated. The received signal from detector 18 may be passed through an amplifier 66, a low pass filter 68, and an analog-to-digital converter 70. The digital data may then be stored in a queued serial module (QSM) 72 (or buffer) for later downloading to RAM 54 as QSM 72 fills up. In one embodiment, there may be multiple separate parallel paths having amplifier 66, filter 68, and A/D converter 70 for multiple light wavelengths or spectra received.

In an embodiment, microprocessor 48 may determine the patient's physiological parameters, such as $SpO_2$, pulse rate, blood pressure, and electromechanical delay using various algorithms and/or look-up tables based on the value of the received signals and/or data corresponding to the light received by detector 18. Signals corresponding to information about patient 40, and particularly about the intensity of light emanating from a patient's tissue over time, may be transmitted from encoder 42 to a decoder 74. These signals may include, for example, encoded information relating to patient characteristics. Decoder 74 may translate these signals to enable the microprocessor to determine the thresholds based on algorithms or look-up tables stored in ROM 52. User inputs 56 may be used to enter information about the patient, such as age, weight, height, diagnosis, medications, treatments, and so forth. In an embodiment, display 20 may exhibit a list of values which may generally apply to the patient, such as, for example, age ranges or medication families, which the user may select using user inputs 56.

The optical signal through the tissue can be degraded by noise, among other sources. One source of noise is ambient light that reaches the light detector. Another source of noise is electromagnetic coupling from other electronic instruments. Movement of the patient also introduces noise and affects the signal. For example, the contact between the detector and the skin, or the emitter and the skin, can be temporarily disrupted when movement causes either to move away from the skin. In addition, because blood is a fluid, it responds differently than the surrounding tissue to inertial effects, thus resulting in momentary changes in volume at the point to which the oximeter probe is attached.

Noise (e.g., from patient movement) can degrade a pulse oximetry signal relied upon by a physician, without the physician's awareness. This is especially true if the monitoring of the patient is remote, the motion is too small to be observed, or the doctor is watching the instrument or other parts of the patient, and not the sensor site. Processing pulse oximetry (i.e., PPG) signals may involve operations that reduce the amount of noise present in the signals or otherwise identify noise components in order to prevent them from affecting measurements of physiological parameters derived from the PPG signals.

It will be understood that the present disclosure is applicable to any suitable signals and that PPG signals are used merely for illustrative purposes. Those skilled in the art will recognize that the present disclosure has wide applicability to other signals including, but not limited to other biosignals (e.g., electrocardiogram, electroencephalogram, electrogastrogram, electromyogram, heart rate signals, pathological sounds, ultrasound, or any other suitable biosignal), dynamic signals, non-destructive testing signals, condition monitoring signals, fluid signals, geophysical signals, astronomical signals, electrical signals, financial signals including financial indices, sound and speech signals, chemical signals, meteorological signals including climate signals, and/or any other suitable signal, and/or any combination thereof.

In an embodiment, microprocessor 48 may also be operable to receive data relating to detected PPG signals and EKG signals for measuring the electrical activation of a patient's heart. For example, microprocessor 48 may receive electromechanical delay information from electromechanical delay monitor 90, which may be coupled to microprocessor 48 through bus 50. Electromechanical delay information may be calculated using constants or parameters from ROM 52, RAM 54, or both and/or may transmit information for storage in ROM 52, RAM 54, or both.

Electromechanical delay monitor 90 receives one or more signals that may be used to measure the electrical activation of a patient's heart. These signals may be obtained from one or more sensors (e.g., EKG sensor 92 (FIG. 1)) coupled to a patient 40. These EKG sensors (not shown) may be incorporated into sensors 12 and 13 or may be separate. In addition to measuring the electromechanical delay of a patient's heart, as described herein, a sensor or pulse oximetry system that includes both pulse oximetry and EKG capabilities may be used to measure and monitor a range of physiological parameters including, but not limited to, $SpO_2$, pulse rate, EKG, respiration rate, respiration effort, blood pressure, and arrhythmia detection.

In some embodiments, microprocessor 48 may also be operable to receive data relating to detected PPG signals, computed blood pressure measurements, sensor elevation, or any other suitable data for use in determining whether monitor 14 or monitor 15 should be recalibrated. For example, microprocessor 48 may receive reference blood pressure measurements from calibration device 80, which may be coupled to microprocessor 48 through bus 50. Upon receiving data from calibration device 80 or any other suitable source, microprocessor 48 may decide whether a recalibration is appropriate and, if so, perform such recalibration. Recalibration may include, for example, computing values for constants or parameters of equations used in determining a patient's blood pressure using the received data, then transmitting the computed constants or parameters to ROM 52, RAM 54, or both for storage.

Figure 3:
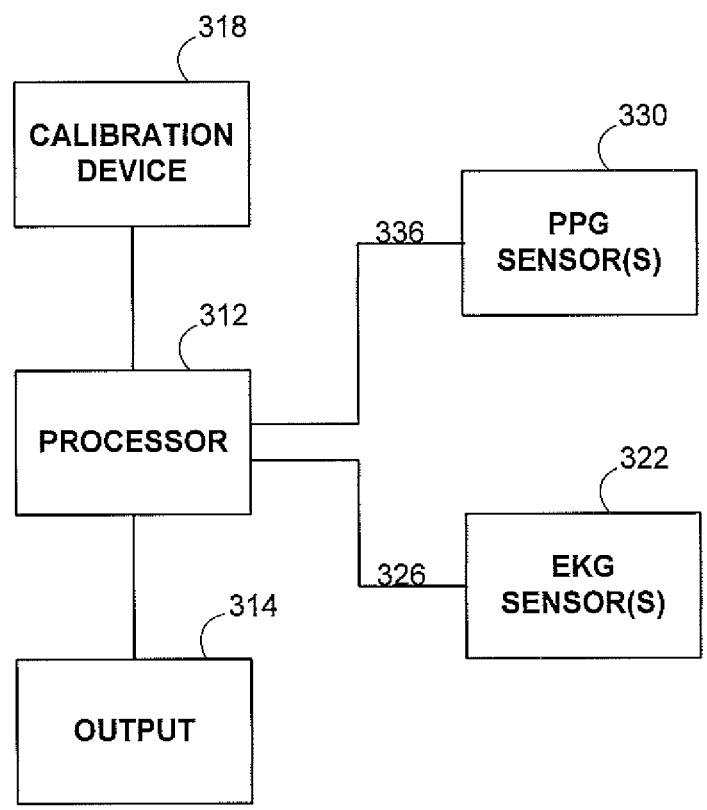
FIG. 3 is a block diagram of an illustrative signal processing system in accordance with an embodiment.

FIG. 3 is an illustrative signal processing system in accordance with an embodiment. In this embodiment, one or more PPG sensors 330 may be used to generate one or more PPG signals 336. One or more EKG sensors 322 may be used to generate one or more EKG signal 326. Signals 326 and 336 may be also be any other suitable signals, such as, for example, biosignals (e.g., electrocardiogram, electroencephalogram, electrogastrogram, electromyogram, heart rate signals, pathological sounds, ultrasound, or any other suitable biosignal), dynamic signals, non-destructive testing signals, condition monitoring signals, fluid signals, geophysical signals, astronomical signals, electrical signals, financial signals including financial indices, sound and speech signals, chemical signals, meteorological signals including climate signals, and/or any other suitable signal, and/or any combination thereof.

In this embodiment, signals 326 and 336 may be coupled to processor 312. Processor 312 may be any suitable software, firmware, and/or hardware, and/or combinations thereof for processing signal 316. For example, processor 312 may include one or more hardware processors (e.g., integrated circuits), one or more software modules, computer-readable media such as memory, firmware, or any combination thereof. Processor 312 may, for example, be a computer or may be one or more chips (i.e., integrated circuits). Processor 312 may perform the calculations associated with measuring electromechanical delay of a patient's heart and/or blood pressure monitoring of the present disclosure. Processor 312 may also perform any suitable signal processing of signal 316 to filter signal 316, such as any suitable band-pass filtering, adaptive filtering, closed-loop filtering, and/or any other suitable filtering, and/or any combination thereof.

Processor 312 may be coupled to one or more memory devices (not shown) or incorporate one or more memory devices such as any suitable volatile memory device (e.g., RAM, registers, etc.), non-volatile memory device (e.g., ROM, EPROM, magnetic storage device, optical storage device, flash memory, etc.), or both. The memory may be used by processor 312 to, for example, store data corresponding to electromechanical delay, including, PPG signal timing, EKG signal timing, current electromechanical delay values and electromechanical delay history. The memory may also be used by processor 312 to, for example, store data corresponding to blood pressure monitoring data, including current blood pressure calibration values, blood pressure monitoring calibration thresholds, and patient blood pressure history. Processor 312 may be coupled to calibration device 318 that may generate or receive as input reference blood pressure measurements for use in calibrating CNIBP calculations.

Processor 312 may be coupled to output 314. Output 314 may be any suitable output device such as, for example, one or more medical devices (e.g., a medical monitor that displays various physiological parameters, a medical alarm, or any other suitable medical device that either displays physiological parameters or uses the output of processor 312 as an input), one or more display devices (e.g., monitor, PDA, mobile phone, any other suitable display device, or any combination thereof), one or more audio devices, one or more memory devices (e.g., hard disk drive, flash memory, RAM, optical disk, any other suitable memory device, or any combination thereof), one or more printing devices, any other suitable output device, or any combination thereof.

It will be understood that system 300 may be incorporated into system 10 (FIGS. 1 and 2) in which, for example, PPG sensors 330 may be implemented using sensors 12 and 13, EKG sensors 322 may be implemented using sensor 92, and processor 312 may be implemented as part of monitor 14, monitor 15, and electromechanical delay monitor 90. In some embodiments, portions of system 300 may be configured to be portable. For example, all or a part of system 300 may be embedded in a small, compact object carried with or attached to the patient (e.g., a watch (or other piece of jewelry) or cellular telephone). In such embodiments, a wireless transceiver (not shown) may also be included in system 300 to enable wireless communication with other components of system 10. As such, system 10 may be part of a fully portable and continuous monitoring solution.

Figure 4:
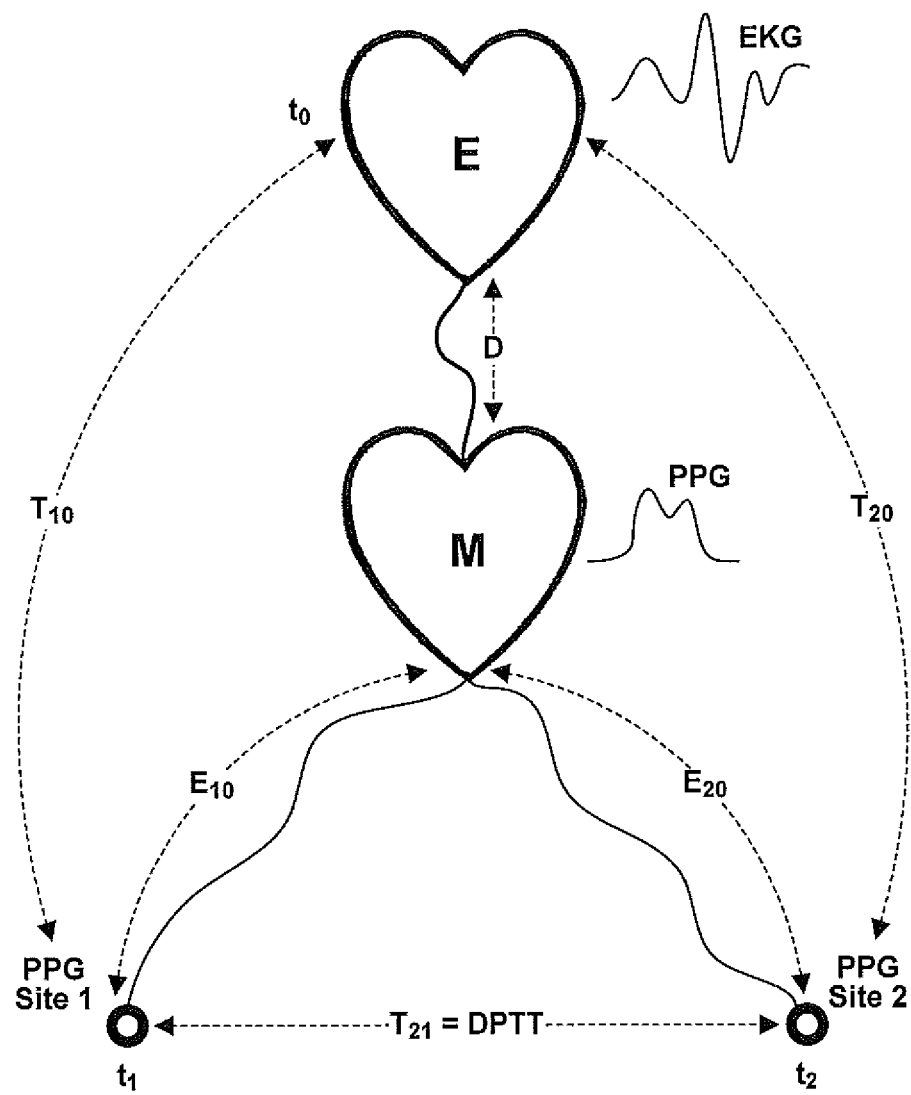
FIG. 4 is an illustrative electromechanical delay timing schematic in accordance with an embodiment.

FIG. 4 is an illustrative electromechanical delay timing schematic in accordance with an embodiment. In this illustrative schematic the electrical activity of the heart is measured using an EKG sensor and the mechanical activity of the heart is measures using two PPG sensors or pulse oximetry sensors located at two different sensor sites. The EKG sensor may be a separate sensor or may be incorporated with the PPG or pulse oximetry sensors. At time $t_0$ heart electrical activity is detected. For example, $t_0$ may correspond to an EKG pulse arrival time. An EKG measures the electrical activity of the heart over time. Typically EKG measurements are performed using multiple skin electrodes placed on various parts of a patient's body. Electrical readings taken from the multiple electrodes may be used to measure the rhythm of the heart. In an embodiment, $t_0$ may correspond to an EKG pulse arrival time at a single electrode, at multiple electrodes, or at all available electrodes. EKG measurements are used herein by way of illustration. It should be understood that any other suitable measurement technique that can detect the electrical activation of the heart may be used. For example, one or more EKG sensors may be used to detect the electrical activation of the heart without using a full EKG setup.

The electromechanical delay between time $t_0$, when electrical activity of the heart is detected, and the mechanical activity of the heart (i.e., beating) may be referred to herein as D. The electromechanical delay of a patient's heart may be a useful parameter in assessing heart performance and may correlate with heart defects and patient outcome. The mechanical activity of the heart may be detected using PPG signals. As described above, PPG signals may be used to measure the timing of individual pulses. At time $t_1$ a pulse corresponding to the heart electrical activity detected at $t_0$ may be measured from a PPG signal obtained using a sensor at a first sensor site. The time difference between $t_0$ and $t_1$ may be referred to as $T_{10}$. $T_{10}$ corresponds to the amount of time from the detection of heart electrical activity until the detection of a pulse at the first sensor site. Time difference $T_{10}$ includes both electromechanical delay D between the heart electrical activity and the heart mechanical activity and $E_{10}$, an amount of time required by a pulse generated by the heart mechanical activity to travel to the first sensor site. Time $t_2$ corresponds to a time at which a pulse corresponding to the heart electrical activity detected at $t_0$ may be measured from a PPG signal obtained using a sensor at a second sensor site. Time difference $T_{20}$ corresponds to the amount of time from the detection of heart electrical activity until the detection of a pulse at the second sensor site. Time difference $T_{20}$ includes both electromechanical delay D between the heart electrical activity and the heart mechanical activity and $E_{20}$, an amount of time required by a pulse generated by the heart mechanical activity to travel to the second sensor site. Time difference $T_{21}$ corresponds to the amount of time between the detection of the pulse at the second sensor site ($t_2$) and the detection of the pulse at the first sensor site ($t_1$). This time difference ($T_{21}$) may also be referred to as the differential pulse transit time (DPTT). As will be described in greater detail below, DPTT may also be used to determine the instantaneous blood pressure of a patient because of a known relationship between DPTT and blood pressure.

In an embodiment, it may be approximated that electromechanical delay D is substantially constant in a given patient while transit times $E_{10}$ and $E_{20}$ are variable, as follows:

$$T_{10}=E_{10}+D \quad (1)$$

$$T_{20}=E_{20}+D \quad (2).$$

In an embodiment, it may also be approximated that these variable transit times scale linearly with DPTT, as follows:

$$E_{10}=A*T_{21} \quad (3)$$

$$E_{20}=B*T_{21} \quad (4).$$

Combining these equations, $$T_{10}=A*T_{21}+D \quad (5)$$

$$T_{20}=B*T_{21}+D \quad (6).$$

Using equation (5) electromechanical delay can be determined by plotting $T_{10}$ against $T_{21}$ to find estimates of A and D (this electromechanical delay estimate may be called $D_1$). Using equation (6) electromechanical delay can be determined by plotting $T_{20}$ against $T_{21}$ to find estimates of B and D (this electromechanical delay estimate may be called $D_2$).

Figure 5:
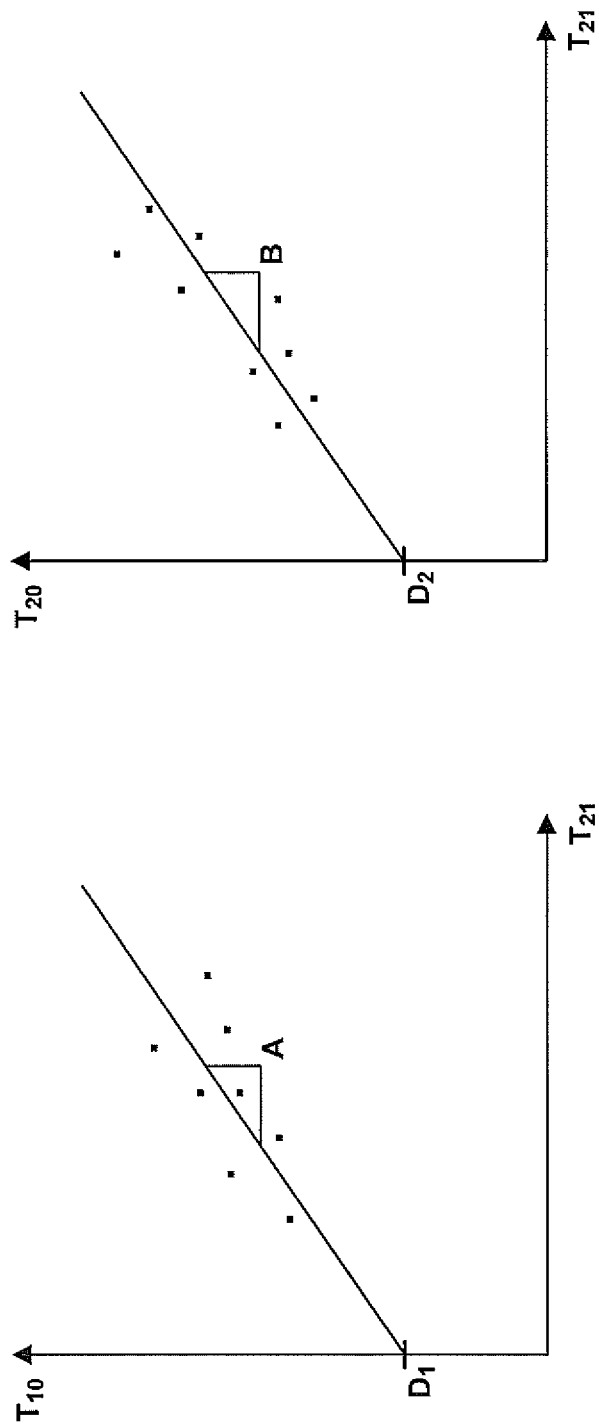
FIG. 5 shows illustrative plots for calculating the electromechanical delay of a patient's heart in accordance with an embodiment.

These plots are illustrated schematically in FIG. 5. In these plots multiple data measurements of $T_{10}$, $T_{20}$, and $T_{21}$ may be used to estimate electromechanical delay. For ease of illustration in FIG. 5, electromechanical delay D is assumed to be substantially constant (relative to the patient transit times and DPTT) and the relationship between transit times ($T_{10}$, $T_{20}$) and DPTT ($T_{21}$) is assumed to be linear. However it should be understood that electromechanical delay may alternatively be assumed to vary with, for example, blood pressure and/or heart rate. Similarly, the variable transit times may be assumed to scale in a nonlinear way with DPTT. In any of these alternatives, values for electromechanical delay may be estimated from multiple data measurements of $T_{10}$, $T_{20}$, and $T_{21}$ and any other physiological parameters of a patient using known data regression and analysis techniques. Further, in an embodiment, the patient may undertake a range of activities during a calibration sequence to increase and/or decrease his or her blood pressure. This may provide a range of data point values that may be used to estimate electromechanical delay.

The two estimates of electromechanical delay D, $D_1$ and $D_2$, may be combined to produce a final estimate of electromechanical delay D. For example, the two estimates may be averaged or may be combined according to a confidence measure. In another example, one of the two estimates may be selected according to a confidence measure or other criteria. For example, the data points measured from one of the sensor sites may provide better (e.g., more stable) data points than the other sensor site. This data collected from this sensor site may be given a higher confidence measure than the other sensor site. Furthermore, while the illustrative electromechanical delay timing schematic of FIG. 4 shows one EKG measurement and two PPG measurements, more EKG and/or PPG measurements may be provided using additional sensors.

Figure 6:
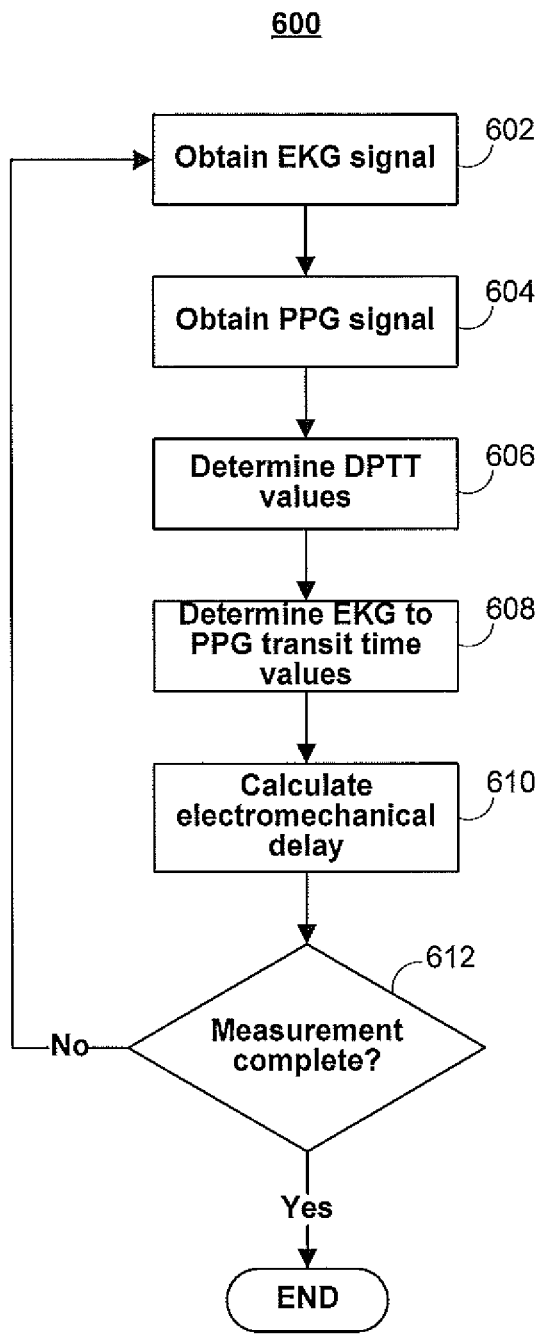
FIG. 6 is a flow chart of an illustrative process for measuring the electromechanical delay of a patient's heart using the pulse oximetry system of FIG. 1 in accordance with an embodiment.

FIG. 6 is a flow chart of an illustrative process 600 for measuring electromechanical delay using the pulse oximetry system 10 of FIG. 1 in accordance with an embodiment. At step 602, an EKG signal may be obtained, for example, using electromechanical delay monitor 90 incorporated into or in communication with the pulse oximetry system 10 (FIG. 1) coupled to sensor 92 (FIG. 1). At step 604, pulse oximetry monitor 14 (FIG. 1) incorporated into or in communication with the pulse oximetry system 10 (FIG. 1) may obtain two or more PPG signal using, for example, sensors 12 and 13 (FIG. 1). At steps 606 and 608, respectively, DPTT values and EKG to PPG transit time values are determined. As discussed above with respect to FIG. 4, these values may be determined based on the obtained EKG and PPG signals. Each set of values may correspond to a single pulse of the heart which includes both electrical and mechanical activity. Multiple sets of values may be determined over multiple pulses to obtain multiple data values. A patient may be instructed to undertake a range of activities to vary their blood pressure in order to obtain a range of data values. The DPTT values and EKG to PPG transit time values may be determined using electromechanical delay monitor 90 (FIG. 1), pulse oximetry monitor 14 (FIG. 1), or any other suitable component or combination of component of pulse oximetry system 10 (FIG. 1). At step 610 electromechanical delay values may be calculated using the values determined at step 606 and 608, for example, in the manner described above with respect to FIGS. 4 and 5. If more than one electromechanical delay value is estimated (e.g., from multiple PPG sensor sites), these multiple electromechanical delay values may be combined or one value may be selected, for example, based confidence measures associated with the values. At step 612 it is determined whether the electromechanical delay value measurement is complete based on, for example, a confidence measure in the calculated value. If the measurement of electromechanical delay is complete, process 600 may end. If additional measurements are desired, process 600 may be repeated. Additionally, process 600 may be repeated at any suitable time. For example, process 600 may be performed periodically (e.g., every 5 to 10 minutes). As another example, process 600 may be performed in response to detecting changes in the monitored physiological characteristics of the patient. Process 600 may be performed in response to detecting a change in the arterial compliance of the patient or in response to a threshold change in the blood pressure of the patient. As another example, process 600 may be performed in response to a request of the device user.

Pulse oximeters, in addition to providing other information, can be utilized for continuous non-invasive blood pressure monitoring. As described in U.S. Pat. No. 6,599,251, the entirety of which is incorporated herein by reference, PPG and other pulse signals obtained from multiple probes can be processed to calculate the blood pressure of a patient. In particular, blood pressure measurements may be derived based on a comparison of time differences between certain components of the pulse signals detected at each of the respective probes. As described in U.S. patent application Ser. No. 12/242,238, entitled "Systems and Methods For Non-Invasive Blood Pressure Monitoring," and filed on Sep. 30, 2008, the entirety of which is incorporated herein by reference, blood pressure can also be derived by processing time delays detected within a single PPG or pulse signal obtained from a single pulse oximeter probe. In addition, as described in U.S. patent application Ser. No. 12/242,867, entitled "Systems and Methods For Non-Invasive Continuous Blood Pressure Determination," and filed on Sep. 30, 2008, the entirety of which is incorporated herein by reference, blood pressure may also be obtained by calculating the area under certain portions of a pulse signal. Further, as described in U.S. patent application Ser. No. 12/242,862, entitled "Systems and Methods For Maintaining Blood Pressure Monitor Calibration," and filed on Sep. 30, 2008, the entirety of which is incorporated herein by reference, a blood pressure monitoring device may be recalibrated in response to arterial compliance changes. Finally, as described in U.S. patent application Ser. No. 12/509,790, entitled "Systems and Methods for Continuous Non-Invasive Blood Pressure Monitoring," and filed on Jul. 27, 2009, the entirety of which is incorporated herein by reference, multiple reference blood pressure values may be used as calibration points for determining a relationship between the blood pressure of a patient and PPG signals.

One benefit of monitoring blood pressure based on PPG signals is that such signals can be obtained in a non-invasive fashion. To continuously monitor blood pressure using a conventional sphygmomanometer, a cuff is repeatedly inflated around a patient's appendage, applying significant pressure. Such repeated pressure can result at a minimum in patient discomfort and potentially in serious injury. In contrast, continuous blood pressure monitoring based on a pulse signal may be achieved merely by placing one or more pulse oximetry probes on appendages and/or other parts of a patient's body.

Some CNIBP monitoring techniques utilize two probes or sensors positioned at two different locations on a subject's body. The elapsed time, T, (i.e., the differential pulse transit time (DPTT)) between the arrivals of corresponding points of a pulse signal at the two locations may then be determined using signals obtained by the two probes or sensors. The estimated blood pressure, P, may then be related to the elapsed time, T, by $$P = a + b \cdot \ln(T) \tag{7}$$

where a and b are constants that may be dependent upon the nature of the subject and the nature of the signal detecting devices. Other suitable equations using an elapsed time between corresponding points of a pulse signal may also be used to derive an estimated blood pressure measurement.

Equation (7) may be used to calculate the estimated blood pressure from the time difference, T, between corresponding points of a pulse signal received by two sensors or probes attached to two different locations of a subject. The value used for the time difference, T, in equation (7) (or in any other blood pressure equation using an elapsed time value between corresponding points of a pulse signal) may also be derived from a signal obtained from a single sensor or probe. In some embodiments, the signal obtained from the single sensor or probe may take the form of a PPG signal obtained, for example, from a CNIBP monitoring system or pulse oximeter.

In an embodiment, constants a and b in equation (7) above may be determined by performing a calibration. The calibration may involve taking a reference blood pressure reading to obtain a reference blood pressure $P_0$, measuring the elapsed time $T_0$ corresponding to the reference blood pressure, and then determining values for both of the constants a and b from the reference blood pressure and elapsed time measurement. Calibration may be performed at any suitable time (e.g., once initially after monitoring begins) or on any suitable schedule (e.g., a periodic or event-driven schedule).

Figure 7:
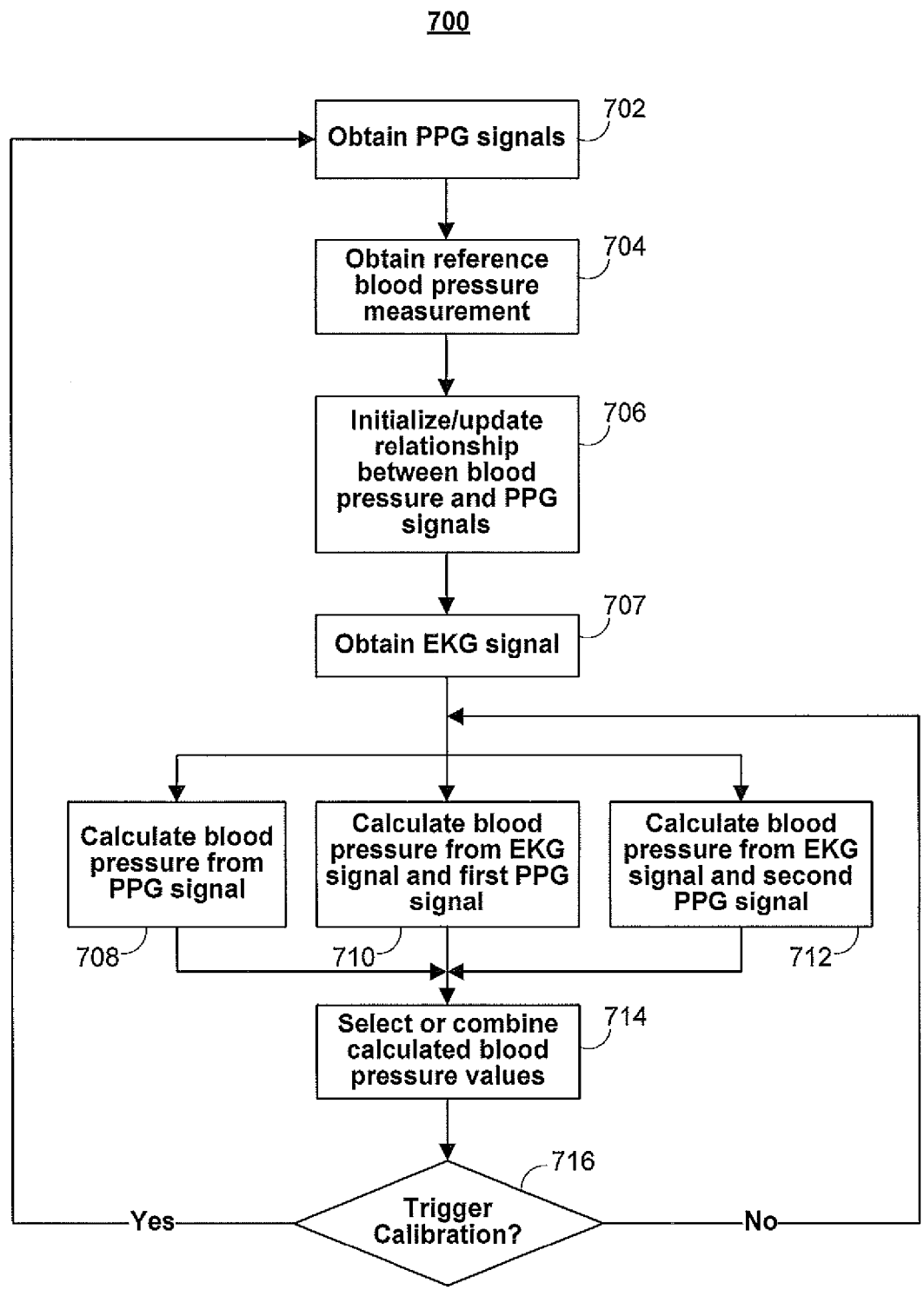
FIG. 7 is a flow chart of an illustrative process for continuous non-invasive blood pressure (CNIBP) monitoring using the electromechanical delay value measured according to the process of FIG. 6 in accordance with an embodiment.

If one of the PPG signals degrades (due to, for example, low perfusion, probe movement, probe positioning, etc.) and is no longer available or is no longer accurate, the system may use an EKG signal and a different PPG signal as a proxy measure of DPTT. FIG. 7 is a flow chart of an illustrative process 700 for monitoring blood pressure using the pulse oximetry system 10 of FIG. 1 or the signal processing system of FIG. 3 in accordance with an embodiment. For purposes of clarity and not limitation, process 700 will be described below as being implemented on pulse oximetry system 10 of FIG. 1. Process 700 begins with blood pressure monitor 15 (FIG. 1) obtaining PPG signals from pulse oximetry system 10 (FIG. 1) at step 702. At step 704, blood pressure monitor 15 (FIG. 1) obtains a reference blood pressure measurement, for example, using calibration device 80 (FIG. 1). For example, calibration device 80 (FIG. 1) may obtain a reference blood pressure measurement using any invasive or non-invasive blood pressure monitoring or measuring system. Such calibration devices may include, for example, an aneroid or mercury sphygmomanometer and occluding cuff 23 (FIG. 1), a pressure sensor inserted directly into a suitable artery of a patient, an oscillometric device or any other device or mechanism used to sense, measure, determine, or derive a reference blood pressure measurement. In some embodiments, calibration device 80 (FIG. 1) may include a manual input device (not shown) used by an operator to manually input reference blood pressure measurements obtained from some other source (e.g., an external invasive or non-invasive blood pressure measurement system). At step 706, blood pressure monitor 15 (FIG. 1) calibrates the relationship between a patient's blood pressure and the PPG signal(s). For example, the relationship may be calibrated: 1) initially after device or monitoring initialization; 2) after a threshold change in monitored physiological characteristics of the patient (e.g., arterial compliance); 3) periodically (e.g., once a day); 4) at the request of the device user; or 5) at any combination of the aforementioned times. At step 707, electromechanical delay monitor 90 (FIG. 1) obtains an EKG signal from pulse oximetry system 10 (FIG. 1). The EKG signal may be used to determine heart electrical activity corresponding to the pulses detected in the PPG signals.

After the relationship between blood pressure and the PPG signals is calibrated, blood pressure may be calculated at one or more of steps 708, 710, and 712. At step 708, blood pressure may be calculated from PPG signals (i.e., based on the DPTT) using the approaches described above for CNIBP monitoring using pulse oximetry. At step 710, blood pressure may be calculated from the EKG signal and the PPG signal obtained from the first sensor site (FIG. 4). For example, using only the PPG signal obtained from the first sensor site, the DPTT may be computed as:

$$(T_{10} - D)/A = T_{21} \quad (8).$$

The calculation of blood pressure performed at step 710 may be performed if the PPG signal obtained from the second sensor site degrades or is otherwise unavailable. At step 712, blood pressure may be calculated from the EKG signal and the PPG signal obtained from the second sensor site (FIG. 4). For example, using only the PPG signal obtained from the second sensor site, the DPTT may be computed as:

$$(T_{20} - D)/B = T_{21} \quad (9).$$

The calculation of blood pressure performed at step 712 may be performed if the PPG signal obtained from the first sensor site degrades or is otherwise unavailable. In other words, blood pressure may be computed at steps 710 and/or 712 using the EKG signal as a proxy for one of the PPG signals using the estimates for A, B, and D (or mathematical equivalents). In equations (8) and (9) the value of electromechanical delay D may be $D_1$, $D_2$, or a function of both $D_1$ and $D_2$. In an embodiment, $D_1$ may be used in equation (8) and $D_2$ may be used in equation (9). In another embodiment, subsequent to calibration, CNIBP may be derived directly from one or both transit times between the EKG and PPG sensors.

At step 714, the blood pressure values calculated in steps 708, 710, and/or 712 may be selected or combined to calculate a blood pressure value. In an embodiment, blood pressure may be calculated at only one of steps 708, 710, and 712, for example, based on the quality of the PPG signals. In another embodiment, DPTT may be calculated at each of steps 708, 710, and 712 to determine the best differential transit time calculation for use in the determination of blood pressure. These DPTT values may be combined or the best value may be selected at step 714. The best DPTT value may be determined based on the quality of the EKG signal, the PPG signals, or both. Furthermore, the difference between the alternate DPTT values may be used as a confidence measure for the DPTT values calculated at step 714. In another embodiment, blood pressure values may be calculated at each of steps 708, 710, and 712. These blood pressure values may be combined or the best value may be selected at step 714. The best blood pressure value may be determined based on the quality of the EKG signal, the PPG signals, or both. Furthermore, the difference between the alternate blood pressure values may be used as a confidence measure for the blood pressure value calculated at step 714. At step 716 it is determined whether to trigger recalibration of the relationship between blood pressure and the PPG signals. Recalibration may be performed, for example, 1) after a threshold change in monitored physiological characteristics of the patient (e.g., arterial compliance); 2) periodically (e.g., once a day); 3) at the request of the device user; or 4) at any combination of the aforementioned times.

Figure 8:
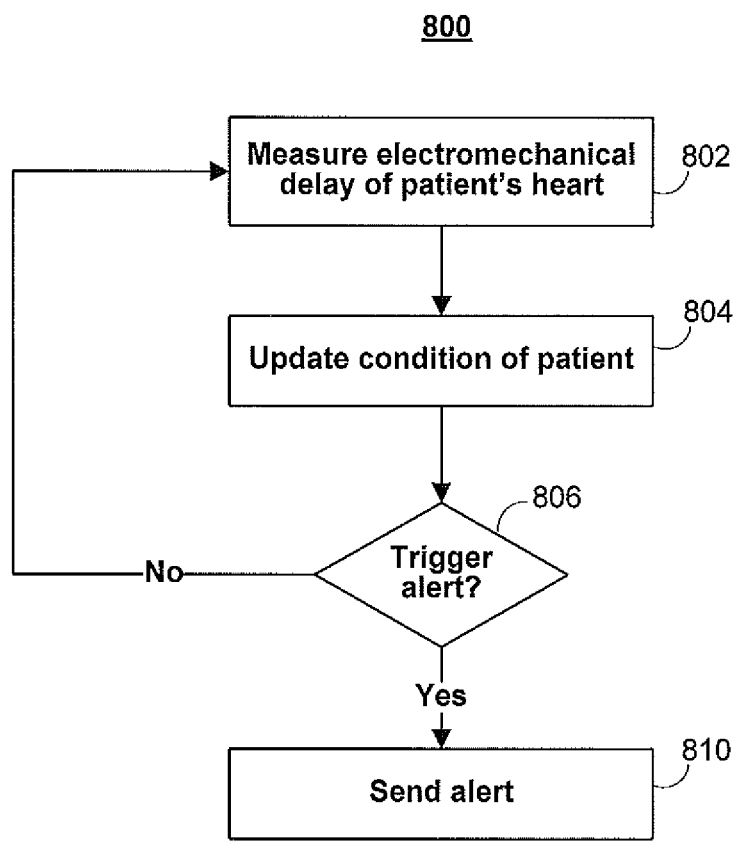
FIG. 8 is a flow chart of an illustrative process for monitoring the electromechanical delay of a patient's heart in accordance with an embodiment.

FIG. 8 is a flow chart of an illustrative process for monitoring the electromechanical delay of a patient's heart in accordance with an embodiment. At step 802 the electromechanical delay of a patient's heart may be measured as described above with respect to FIGS. 4-6. At step 804 the condition of the patient may be updated based on the measured electromechanical delay. The electromechanical delay value may be used to assess heart performance and may correlate with heart defects and patient outcomes. Furthermore, changes in the measured electromechanical delay values may be indicative of changes in a patient's condition such as, for example, impending cardiac failure. At step 806, it is determined whether to trigger an alert based on the condition of the patient. For example, alerts may be triggered whenever the measured electromechanical delay exceeds a predetermined value or whenever the measured electromechanical delay changes by more than a predetermined value. At step 810, an alert may be sent. The alert may include a message or indication displayed on blood pressure monitor 15 (FIG. 1), pulse oximetry monitor 14 (FIG. 1), electromechanical delay monitor 90 (FIG. 1), multi-parameter patient monitor 26 (FIG. 1), and/or any other suitable component of pulse oximetry system 10 (FIG. 1) or the signal process system of FIG. 3. The alert may also include an audio alert using, for example, speaker 22 (FIG. 1). The alert may also be transmitted to other devices. For example, an alert may be transmitted using any suitable wired or wireless protocol to a central monitoring facility. In an embodiment, electromechanical delay monitor 90 (FIG. 1) and components of pulse oximetry system 10 (FIG. 1) may be incorporated into a portable device that may perform the steps of process 800. This portable device may monitor the electromechanical delay of a patient's heart and may wirelessly send updates and/or alerts to a monitoring facility that may be used to assess the health of cardiac function. If an alert is not triggered at step 806, processes 800 may be repeated in order to monitor changes in the electromechanical delay value.

The foregoing is merely illustrative of the principles of this disclosure and various modifications can be made by those skilled in the art without departing from the scope and spirit of the disclosure. The above described embodiments are presented for purposes of illustration and not of limitation. The present disclosure also can take many forms other than those explicitly described herein. Accordingly, it is emphasized that the disclosure is not limited to the explicitly disclosed methods, systems, and apparatuses, but is intended to include variations to and modifications thereof which are within the spirit of the following claims.

What is claimed is:

1. A system for measuring electromechanical delay of the heart of a patient, the system comprising:
   a first PPG sensor configured for attaching to the patient at a first location and for generating a first PPG signal from the first location;
   a second PPG sensor configured for attaching to the patient at a second location and for generating a second PPG signal from the second location, wherein the first and second locations are distal to the heart;
   an EKG sensor configured for attaching to the patient and for generating an EKG signal;
   a processor coupled to the first and second PPG sensors and the EKG sensor, wherein the processor is capable of:
      determining a plurality of differential pulse transit time (DPTT) values, wherein each of the plurality of DPTT values is based on both the first and second PPG signals, wherein the first and second PPG signals indicate a pulse wave at the respective first and second locations distal to the heart, determining at least one EKG to PPG transit time value based at least in part on the EKG signal and the first PPG signal, determining a calibration coefficient using at least one DPTT value of the plurality of DPTT values and the at least one EKG to PPG transit time value, and calculating an electromechanical delay value based at least in part on another DPTT value of the plurality of DPTT values and the determined calibration coefficient; and an output device coupled to the processor.

2. The system of claim 1, wherein the at least one EKG to PPG transit time value comprises a substantially constant electromechanical delay component and a variable pulse transit time component, wherein the variable pulse transit time component scales substantially linearly with DPTT.

3. The system of claim 2, wherein the relationship between the at least one EKG to PPG transit time value and the at least one DPTT value is $$E = A \cdot T + D$$

or a mathematical equivalent thereof, wherein E is an EKG to PPG transit time value, T is a DPTT value, D is the electromechanical delay value, and A is the calibration coefficient.

4. The system of claim 1, wherein the processor is further capable of:

determining a further EKG to PPG transit time value based at least in part on the EKG signal and the second PPG signal; and determining a calibration second coefficient based at least in part on the at least one DPTT value of the plurality of DPTT values and the further EKG to PPG transit time value.

5. The system of claim 4, wherein the processor is further capable of determining a third calibration coefficient based at least in part on the at least one DPTT value of the plurality of DPTT values and the EKG to PPG transit time values determined from the first and the second PPG signals.

6. The system of claim 1, wherein the processor is further capable of assessing a condition of the patient's heart based at least in part on the electromechanical delay value.

7. The system of claim 6, wherein the processor is further capable of:

monitoring the electromechanical delay value over time;

determining a change in the electromechanical delay value; and triggering the output device to generate an alert.

8. The system of claim 1, wherein the processor is further capable of calculating a blood pressure value of the patient based on at least one of: (a) the plurality of DPTT values and (b) the electromechanical delay value and the at least one EKG to PPG transit time value.

9. The system of claim 8, wherein the processor is further capable of:

detecting a signal degradation of at least one of the first and second PPG signals; and calculating a blood pressure value of the patient based on the electromechanical delay value and EKG to PPG transit time values based on at least one other PPG signal in response to detecting the signal degradation.

10. A method for measuring electromechanical delay of the heart of a patient, the method comprising:

obtaining a first PPG signal using a first PPG sensor that is attached to the patient at a first location;

obtaining a second PPG signal using a second PPG sensor that is attached to the patient at a second location, wherein the first and second locations are distal to the heart;

obtaining an EKG signal using an EKG sensor that is attached to the patient;

determining, using a processor, a plurality of differential pulse transit time (DPTT) values, wherein each of the plurality of DPTT values is based on both the first and second PPG signals, wherein the first and second PPG signals indicate a pulse wave at the respective first and second locations distal to the heart;

determining, using the processor, at least one EKG to PPG transit time value based at least in part on the EKG signal and the first PPG signal;

determining, using the processor, a calibration coefficient using at least one DPTT value of the plurality of DPTT values and the at least one EKG to PPG transit time value; and calculating, using the processor, an electromechanical delay value based at least in part on another DPTT value of the plurality of DPTT values and the determined calibration coefficient.

11. The method of claim 10, wherein the at least one EKG to PPG transit time value comprises a substantially constant electromechanical delay component and a variable pulse transit time component, wherein the variable pulse transit time component scales substantially linearly with DPTT.

12. The method of claim 11, wherein the relationship between the at least one EKG to PPG transit time and the at least one DPTT value is $$E = A \cdot T + D$$

or a mathematical equivalent thereof, wherein E is an EKG to PPG transit time value, T is a DPTT value, D is the electromechanical delay value, and A the calibration coefficient.

13. The method of claim 10, further comprising:

determining a further EKG to PPG transit time value based at least in pan on the EKG signal and the second PPG signal; and determining a second calibration coefficient based at least in part on the plurality of DPTT values and the further EKG to PPG transit time value.

14. The method of claim 13, further comprising determining a third calibration coefficient based at least in part on the at least one DPTT value of the plurality of DPTT values and the EKG to PPG transit time values determined from the first and the second PPG signals.

15. The method of claim 10, further comprising assessing a condition of the patient's heart based at least in part on the electromechanical delay value.

16. The method of claim 15, further comprising:

monitoring the electromechanical delay value over time;

determining a change in the electromechanical delay value; and triggering the output device to generate an alert.

17. The method of claim 10, further comprising calculating a blood pressure value of the patient based on at least one of: (a) the plurality of DPTT values and (b) the electromechanical delay value and the at least one EKG to PPG transit time value.

18. The method of claim 17, further comprising:

detecting a signal degradation of at least one of the first and second PPG signals; and calculating a blood pressure value of the patient based on the electromechanical delay value and EKG to PPG transit time values based on at least one other PPG signal in response to detecting the signal degradation.

19. A non-transitory computer-readable medium for use in measuring electromechanical delay of the heart of a patient, the non-transitory computer-readable medium comprising:
computer program instructions recorded thereon for causing a pulse oximeter to:
obtain a first PPG signal from a first PPG sensor configured for attaching to the patient at a first location;
obtain a second PPG signal from a second PPG sensor configured for attaching to the patient at a second location, wherein the first and second locations are distal to the heart;
obtain an EKG signal from an EKG sensor configured for attaching to the patient;
determine a plurality of differential pulse transit time (DPTT) values, wherein each of the plurality of DPTT values is based on both the first and second PPG signals, wherein the first and second PPG signals indicate a pulse wave at the respective first and second locations distal to the heart;
determine at least one EKG to PPG transit time value based at least in part on the EKG signal and the first PPG signal;
determine a calibration coefficient using at least one DPTT value of the plurality of DPTT values and the at least one EKG to PPG transit time value; and
calculate an electromechanical delay value based at least in part on another DPTT value of the plurality of DPTT values and the calibration coefficient.

20. The system of claim 1, wherein the processor is further capable of:
determining a plurality of EKG to PPG transit time values based at least in part on the EKG signal and the first PPG signal, wherein determining the calibration coefficient comprises performing data regression analysis of a data set based on at least some DPTT values of the plurality of DPTT values and the plurality of EKG to PPG transit time values.

21. The system of claim 1, wherein one or more DPPT values of the plurality of DPTT values are determined over time when the patient is undertaking at least one activity for increasing or decreasing blood pressure of the patient.

22. The system of claim 1, wherein each DPTT value of the plurality of DPTT values is determined at a different time.

23. The method of claim 10, wherein each DPTT value of the plurality of DPTT values is determined at a different time.

* * * * *